United States Patent [19]
Iwamasa et al.

[11] Patent Number: 5,560,046
[45] Date of Patent: Oct. 1, 1996

[54] LUMBAR SUPPORT BELT WITH SUSPENDERS AND ELASTIC SECTIONS HAVING DIFFERENT ELASTICITIES

[76] Inventors: Yukio Iwamasa, 5203 Deeboyar Ave., Lakewood, Calif. 90712; Joseph R. Noriega, 901 W. Whittier Blvd., Montebello, Calif. 90640

[21] Appl. No.: 218,628

[22] Filed: Mar. 25, 1994

[51] Int. Cl.$^6$ ............................................. A41F 3/00
[52] U.S. Cl. ........................ 2/328; 128/101.1; 602/19
[58] Field of Search .................. 2/311, 312, 338, 2/336, 328, 321, 322, 44; 128/95, 196.1, 100.1, 101.1, 121.1; 482/105, 106; 602/19; 450/131

[56] References Cited

U.S. PATENT DOCUMENTS

| | | |
|---|---|---|
| 756,177 | 3/1904 | Mills . |
| 1,418,371 | 6/1922 | Foster . |
| 1,558,228 | 10/1925 | Botkin . |
| 2,097,159 | 10/1937 | Kendrick ................................ 450/131 |
| 2,351,158 | 6/1944 | Stelzer . |
| 3,554,190 | 1/1971 | Kaplan ........................................ 2/44 |
| 3,603,316 | 9/1971 | Lehman ...................................... 2/312 |
| 4,341,331 | 7/1982 | McDougall . |
| 4,440,525 | 4/1984 | Perla . |
| 4,579,265 | 4/1986 | Schiller . |
| 4,718,585 | 1/1988 | Atkins, Sr. . |
| 4,966,320 | 10/1990 | DeSantis et al. . |
| 5,038,760 | 8/1991 | Osborn .......................................... 2/44 |
| 5,147,261 | 9/1992 | Smith et al. .............................. 2/338 |
| 5,241,704 | 9/1993 | Sydor ........................................ 2/338 |
| 5,257,419 | 11/1993 | Alexander ................................ 2/338 |
| 5,349,706 | 9/1994 | Keer ............................................ 2/44 |
| 5,388,274 | 2/1995 | Glover et al. ............................... 2/44 |

FOREIGN PATENT DOCUMENTS

| 275109 | 8/1927 | United Kingdom ...................... 2/312 |
|---|---|---|

*Primary Examiner*—C. D. Crowder
*Assistant Examiner*—Gloria Hale
*Attorney, Agent, or Firm*—David Weiss

[57] ABSTRACT

A lumbar support belt in which vertical displacement with respect to the wearer's body is precluded, or at least significantly lessened. The belt further includes an improved elastic support section for promoting a more even distribution of pressure against a wearer's lumbar region. In addition, the back belt is provided with detachable suspenders, and the suspenders and belt are configured for implementing correct installation of the suspenders to the belt.

10 Claims, 1 Drawing Sheet

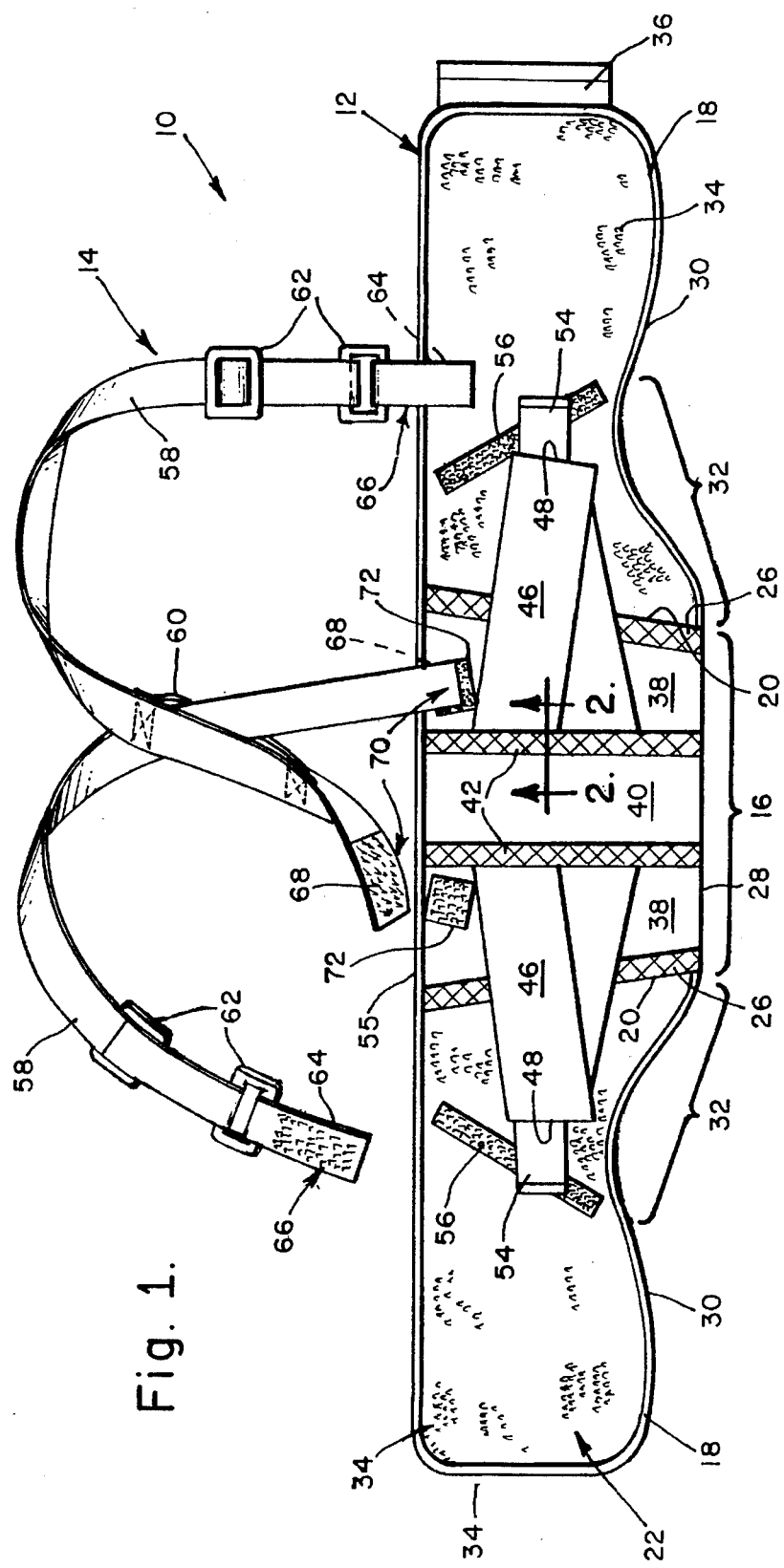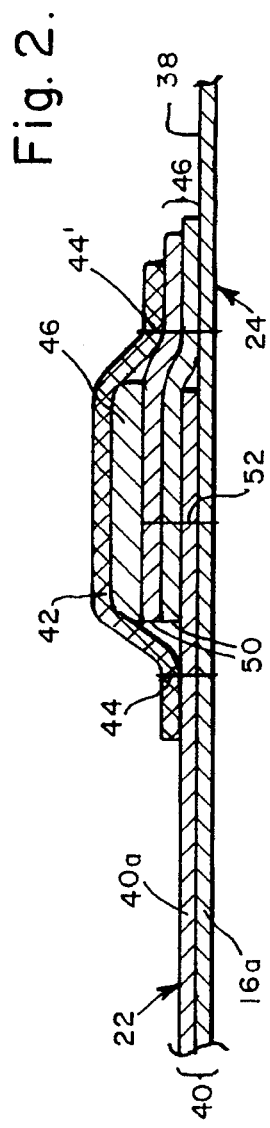

LUMBAR SUPPORT BELT WITH SUSPENDERS AND ELASTIC SECTIONS HAVING DIFFERENT ELASTICITIES

BACKGROUND OF THE INVENTION

This invention relates to lumbar support belts, and more particularly to a lumbar support belt with improved positional stability, support and convenience when worn by person.

Lumbar (or sacro lumbar) support belts (also commonly known as back belts or lifting belts) are well known devices which are worn about a person's lumbar region for promoting comfort and for decreasing the likelihood of certain types of back injury. Such belts are popularly worn by persons while engaging in physical activities, at work or at play.

Lumbar support belts typically include a laterally elastic support section for engaging the person's back generally in the lumbar region when the belt is worn, and two end panels respectively secured to the elastic support section along laterally opposite ends thereof. The end panels include securing means for releasably securing the end panels to one another generally in front of the person when the belt is worn, and in securing the end panels the person coerces the elastic section to stretch for applying supportive pressure to the person's lumbar region. Adjustable suspenders are permanently secured to the back belt for preventing the belt from dropping to the floor when the belt is loosened by the wearer.

A recurring problem with prior art lumbar support belts concerns a tendency of such belts when worn to travel or become displaced upwardly on the person's body, and in so doing to decrease the effectiveness of the lumbar support function of the belt. Such positional displacement is most pronounced when the wearer bends, squats or kneels, and the wearer is required to pull downwardly on the belt after such body motions for restoring the lumbar support effectiveness of the belt.

SUMMARY OF THE INVENTION

The present invention provides a lumbar support belt in which such positional displacement or instability is precluded, or at least significantly lessened, by such activities. The present belt, in addition, provides an improvement to the belt's elastic support section for promoting a more even pull by such section and thereby increasing effectiveness of the belt's support function. Further, the present belt is provided with detachable suspenders so that the belt may be worn without suspenders if desired; and the suspenders and belt of the present invention are configured for implementing correct installation of the suspenders to the belt while having the capability of adapting to the anatomy of a particular wearer.

Briefly described, the lumbar support belt according to the present invention, for being worn by a person, comprises in combination: a laterally elastic support section for engaging the person's back generally in the lumbar region when the belt is worn, such elastic support section having a lower edge; and two end panels respectively secured to the elastic support section along laterally opposite ends thereof, the end panels including securing means for releasably securing the end panels to one another generally in front of the person when the belt is worn, each of the end panels having a lower edge ascending from the lower edge of the elastic support section for precluding engagement of the end panels with the person's thighs when the belt is worn.

The laterally elastic support section includes two elastic panels of substantially equal elasticity and a third panel laterally separating the two elastic panels and of elasticity less than the elasticity of the two elastic panels. The belt further includes two laterally elastic members each having one end thereof secured to the elastic support section along respective laterally opposite ends of the third panel, the members including securing means for releasably securing the other ends of the members to the two end panels respectively. In a preferred embodiment, the three elastic panels of the elastic support section are constructed of similar laterally elastic fabric material, and each of the two laterally separated elastic panels comprises a single layer thereof and the third elastic panel comprises a double layer thereof.

The lumbar support belt further includes cooperative fastening means of one type on each of the belt's end panels; cooperative fastening means of another type on the elastic support section, preferably on each of the two laterally separated panels of the elastic support section; and a pair of suspenders including two straps, each strap having at one end thereof cooperative fastening means for cooperating with the cooperative fastening means of the one type for releasably securing the one ends of the straps to the end panels respectively, each strap having at another end thereof cooperative fastening means for cooperating with the cooperative fastening means of the other type for releasably securing such other ends of the straps to the elastic support section and preferably to such section's laterally separated panels respectively. The cooperative fastening means of the one type includes loop-pile fastening means; the cooperative fastening means of the other type includes hook-pile fastening means; the cooperative fastening means on the one ends of the straps includes hook-pile fastening means; and the cooperative fastening means on the other ends of the straps includes loop-pile fastening means. Such cooperative loop-pile and hook-pile fasteners are preferably of the kind marketed under the trademark VELCRO®.

BRIEF DESCRIPTION OF THE DRAWINGS

The novel features which are believed to be characteristic of the invention, together with further advantages thereof, will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

FIG. 1 is an elevation view of the outer side of a preferred embodiment of a lumbar (or sacro lumbar) support belt according to the present invention, shown extending along its lateral dimension; and FIG. 2 is a sectional view of a fragment of the belt of FIG. 1, taken along the line 2—2 in the direction of the appended arrows, greatly enlarged for clarity.

DESCRIPTION OF THE PREFERRED EMBODIMENT

Turning to FIG. 1, there is shown a preferred embodiment of a lumbar support belt assembly 10, including a lumbar (or sacro lumbar) support belt or back belt 12 to be worn generally about a person's lumbar region and waist, and a pair of suspenders 14 removably securable to the belt 12 for being worn from the person's shoulders. The back belt 12 includes a laterally elastic fabric support section 16 and two substantially non-elastic end panels 18 respectively secured to the elastic support section 16 along laterally opposite ends 20 of the elastic support section 16. As used herein, the term "lateral" as applied to the belt 12 indicates the generally longitudinal dimension of the belt 12 as intended to be worn by a person about his/her waist, i.e. the horizontal dimension as viewed in the drawing of FIG. 1. When worn, the back belt 12 may be considered as having an outer surface or side 22 (i.e., a surface disposed away from the wearer's body and as viewed in FIG. 1) and an inner surface or side 24 (i.e., a surface or side disposed toward or facing the wearer's body, not shown in FIG. 1 although a fragment thereof is shown in FIG. 2).

The end panels 18 may be respectively secured to the elastic support section 16 along the laterally opposite ends 20 thereof in conventional manner, as by sandwiching an end of a panel 18 and an end of the elastic section 16 between a pair of superposed strips of webbing (only one of the pair being shown in FIG. 1 with the reference numeral 26, the other webbing strip of the pair being on the inner side 24 of the belt 12) and sewing the pair of webbing strips together along their edges. Each sewn generally vertically disposed webbing strip 26 forms a pocket or enclosure with the other strip of the pair, and each pocket contains a generally vertically disposed stiffening rib or stay (not shown), of material such as spring steel.

The elastic support section 16 includes a lower edge 28 (as viewed in FIG. 1 and when the belt 12 is worn) generally extending in the lateral dimension. Each of the non-elastic end panels 18 includes a lower edge 30 laterally ascending from the lower edge 28 of the elastic support section 16, preferably as an ascending curve 32, defining a contoured portion of each end panel 18 rising above the wearer's thighs when the belt 12 is worn. Such ascending configuration of the lower edges 30 of the end panels 18 on each side of the elastic support section 16 precludes the end panels 18 from engaging the wearer's thighs when the belt 12 is worn, and in particular when the wearer bends, squats or kneels. Such avoidance of the wearer's upper thighs by the contoured lower edges 30 of the end panels 18 prevents the back belt 12 from travelling or becoming displaced upwardly on the wearer's body as a result of such maneuvers, or at least significantly decreases a propensity of the back belt 12 to do so.

Each of the non-elastic end panels 18 contains or has included on its outer side 22 a loop-pile material which may be utilized as a cooperative loop-pile fastening material, indicated generally by the reference numeral 34. When the back belt 12 is worn generally about a person's waist with the elastic support section 16 against the person's back generally in his/her lumbar region, the belt 12 may be fastened while stretching the elastic section 16 for pressing against the wearer's back. This is accomplished by forwardly pulling the end panels 18 while overlapping portions of the end section 18 to one another by releasably fastening a closure tab 36 (secured to one of the end sections 18) containing hook-pile fastening material on its inner side (i.e., into the plane of the drawing as viewed in FIG. 1, not shown) cooperating with the loop-pile fastening material 34 on the other (or overlapped) end panel 18. Such loop-pile material and hook-pile material complement or cooperate with one another for providing a releasable fastener, as is well known and such as marketed under the trademark VELCRO®.

Considering FIG. 2 along with FIG. 1, a feature of the preferred back belt embodiment 12 of the present invention includes an improved laterally elastic support section 16, for distributing the pressure upon the wearer's lumbar region more evenly than has been experienced with back belts of the prior art. In such prior art back belts, the laterally elastic belt section (analogous to the belt section 16 of FIG. 1) usually comprises a single ply or layer of a laterally elastic fabric effectively divided into three laterally arranged panels (analogous, as viewed in FIG. 1, to the two elastic panels 38 separated by a third elastic panel 40) by two vertically disposed sewn strips of webbing with contained vertically disposed stiffeners or stays (analogous to the webbing strips 42 sewn with stitches 44, 44' to elastic fabric layer 16a comprising one layer of elastic section 16 of the present invention, with a vertically disposed stiffener or stay 46 contained within the pocket enclosure formed by the sewn webbing strip 42). The back belt 12 of the present invention-as well as back belts of the prior art-further includes two laterally elastic members 46 each having one end secured to the intermediate elastic panel of the laterally elastic support section, as represented in FIG. 1 by the two elastic strips 46 each angularly folded upon itself from a fold line 48 defining a free end thereof with the other end of each member 46 secured to the elastic support section 16 along laterally opposite ends of the intermediate panel 40, such as by stitches 52 as shown in FIG. 2.

In contrast to the single ply or layer of elastic material comprising the laterally elastic support section of the black belts of the prior art, however, the laterally elastic support section 16 of the back belt 12 of the present invention includes an intermediate panel 40 comprising two plies or a double layer of elastic fabric material while the two laterally separated elastic panels 38 each comprise one ply or a single layer of the elastic fabric material. As indicated in FIG. 2, the elastic support section 16 is comprised of a layer of elastic material 16a extending along the full lateral dimension of the elastic support section 16, and a second layer 40a of similar elastic material superposed (as viewed in FIG. 2) and coextensive with the intermediate elastic panel 40, the layer 40a secured along its laterally separated ends to the first elastic layer 16a and the webbing strip 42 by stitches 44, 44', 52. Accordingly, in the laterally elastic support section 16 of the present invention, the two laterally separated elastic panels 38 are of substantially equal lateral elasticity while the third or intermediate elastic panel 40 laterally separating the two panels 38 is of elasticity less than the elasticity of the two elastic panels 38.

The free ends 48 of the elastic members 46 have respectively secured thereto fastening tabs 54 containing cooperative hook-pile fastening material on their inner sides (not shown) for respectively cooperating with the cooperative loop-pile fastening material 34 on the outer sides 22 of the end sections 18, for releasably securing the ends 48 of the members 46 respectively to the two end panels 18 when the belt 12 is worn. Such securement is effected after the belt 12 has been placed about the wearer's lumbar area and waist and the closure tab 36 has been fastened to the overlapped end section 18, by forwardly pulling and stretching the elastic members 46 and causing the hook-pile material of the fastening tabs 54 to cooperatively engage the loop-pile material 34 on the non-elastic end panels 18 while the elastic members 46 are in a stretched condition. This causes some lateral stretching of the intermediate elastic panel 40 of the elastic belt section 16. Since the intermediate section 40 (comprising two plies of similar elastic fabric material) is of lesser elasticity than the two separated elastic panels 38

(comprising a single ply of similar elastic fabric material), the amount of lateral stretching of the intermediate section 40 is less than would normally result with a prior art back belt (having an elastic support section comprising three single ply panels of similar elastic fabric material), causing a more even distribution of pressure by the back belt 12 against the wearer's lumbar region.

One example of a laterally elastic fabric material which may be utilized for constructing the laterally elastic support section 16, is a nine inch elastic knit material marketed by South Carolina Elastic Company under the designation 2N15289KBLK288R. In one example of a back belt 12 utilizing such elastic fabric material, the height of the section 16 was approximately 9 inches, and the nominal width (i.e. in the lateral dimension) of each of the three panels 38, 40 was approximately 3 inches although the width of each panel 38 was less along the lower edge 28 than along the upper edge 55 of the section 16 as may be noted in FIG.1. The lateral dimension of each of the elastic members 46 was approximately 8 inches, constructed of 3 inch wide elastic fabric strip material.

Stiffener members or stays are contained in pockets or enclosures formed by fabric strips 26 respectively secured to the end panels 18, inclined from vertical as viewed in FIG. 1, and covered with cooperative loop-pile fastening material 34.

Another feature of the preferred back belt assembly 10 of the present invention includes the suspenders 14 which are easily removable from and securable to the back belt 12. The pair of suspenders 14 includes two fabric straps 58 of substantially equal width and length, with one of the straps 58 having a loop section 60 sewn thereto for loosely retaining the other strap 58 inserted therethrough. The length of each strap 58 may be adjusted, for example by well known adjustment slide or buckle devices 62. The fabric suspender straps may be webbing, although it is preferred that each of the straps 58 comprise a fabric material which is elastic along the strap's longitudinal dimension.

For proper securement of the suspenders 14 to the back belt 12 when worn, the adjustment buckle devices 62 are situated in front of the wearer while the suspender's loop section 60 is positioned rearwardly of the wearer. A pad of cooperative hook-pile fastening material 64 is respectively secured to each strap 58 at the strap's front end 66, i.e. the end 66 in the vicinity of the adjustment buckle device 62, for cooperatively engaging the loop-pile fastening means 34 on the non-elastic end panels 18 and for removably securing the forward ends 66 of the straps 58 to the end panels 18 respectively. A pad of cooperative loop-pile fastening material 68 is secured to each strap 58 at the other end 70 thereof, i.e. at the ends in the vicinity of the loop section 60, for cooperatively engaging respective pads of outwardly facing cooperative hook-pile fastening material 72 secured to the elastic support section 16 and preferably to the respective laterally separated elastic panels 38 in the vicinity of the upper edge 55 of the section 16, for removably securing the rearward ends 70 of the straps 58 to the elastic support section 16. It may be appreciated that, by means of the arrangement just described, the suspenders 14 may be secured to the back belt 12 only in one configuration, i.e. with the adjustment buckle devices 62 forwardly of the wearer (i.e., anywhere along the end panels 18) and the loop section 60 rearwardly of the wearer. Further, in contrast to the prior art back belt assemblies wherein the suspenders are permanently secured to the back belt, the back belt assembly 10 of the present invention permits the back belt 12 of the present invention to be worn with or without the suspenders 14 of the present invention secured thereto, and permits the wearer to secure or remove the suspenders 14 to or from the back belt 12 as desired. An additional advantage of the present invention is the capability of securing the forward ends 66 of the suspender straps 58 to any location on or along the end panels 18 as may be comfortable to or may suit the anatomy of a particular wearer.

Thus, there has been described an improved lumbar support belt assembly in which vertical displacement of the back belt is precluded or at least significantly lessened, which includes an improved elastic support section, and which includes detachable suspenders configured for implementing correct installation of the suspenders to the belt. Other embodiments and modifications of the embodiment shown herein may be developed without departing from the essential characteristics thereof. Accordingly, the invention should be limited only by the scope of the claims listed below.

We claim:

1. A lumbar support belt for being worn by a person, comprising in combination:

a laterally elastic support section for engaging the person's back generally in the lumbar region when the belt is worn, said elastic support section having a lower edge and including two elastic panels of substantially equal elasticity and a third elastic panel laterally separating said two panels and of elasticity less than the elasticity of said two elastic panels; and two end panels respectively secured to said elastic support section along laterally opposite ends thereof, said end panels including securing means for releasably securing said end panels to one another generally in front of the person when the belt is worn, each of said end panels having a lower edge ascending from said lower edge of said elastic support section for precluding engagement of said end panels with the person's thighs when the belt is worn.

2. The lumbar support belt according to claim 1:

further including two laterally elastic members each having one end thereof secured to said elastic support section along respective laterally opposite ends of said third panel, said members including securing means for releasably securing the other ends of said members to said two end panels respectively; and wherein said elastic panels of said elastic support section are constructed of similar elastic fabric material, each of said two laterally separated elastic panels comprises a single layer thereof and said third elastic panel comprises a double layer thereof.

3. The lumbar support belt according to claim 1, further including:

cooperating fastening means of one type on each of said end panels;

cooperating fastening means of another type on each of two laterally separated panels of said elastic support section; and two suspender straps, each said strap having at one end thereof cooperative fastening means for cooperating with said cooperative fastening means of said one type for releasably securing said one ends of said straps to said end panels respectively, each said strap having at another end thereof cooperative fastening means for cooperating with said cooperative fastening means of said other type for releasably securing said other ends of said straps to said laterally separated panels respectively.

4. The lumbar support belt according to claim 3, wherein:

said cooperative fastening means of said one type includes loop-pile fastening means;

said cooperative fastening means of said other type includes hook-pile fastening means;

said cooperative fastening means on said one ends of said straps includes hook-pile fastening means; and said cooperative fastening means on said other ends of said straps includes loop-pile fastening means.

5. In a lumbar support belt for being worn by a person, the combination comprising:

a laterally elastic support section for engaging the person's back generally in the lumbar region including two elastic panels of substantially equal elasticity and a third elastic panel laterally separating said two elastic panels and of elasticity less than the elasticity of said two elastic panels; and two end panels respectively secured to said elastic support section along laterally opposite ends thereof, said end panels including securing means for releasably securing said end panels to one another generally in front of the person when the belt is worn.

6. The lumbar support belt according to claim 5, further including two laterally elastic members each having one end thereof secured to said elastic support section along respective laterally opposite ends of said third panel, said members including securing means for releasably securing the other ends of said members to said two end panels respectively; and wherein said elastic panels of said elastic belt section are constructed of similar elastic fabric material, each of said two laterally separated elastic panels comprises a single layer thereof and said third elastic panel comprises a double layer thereof.

7. The lumbar support belt according to claim 6, further including:

cooperative fastening means of one type on each of said end panels;

cooperative fastening means of another type on each of said two laterally separated elastic panels of said support section; and two suspender straps, each said strap having at one end thereof cooperative fastening means for cooperating with said cooperative fastening means of said one type for releasably securing said one ends of said straps to said end panels respectively, each said strap having at another end thereof cooperative fastening means for cooperating with said cooperative fastening means of said other type for releasably securing said other ends of said straps to said laterally separated elastic panels respectively.

8. The lumbar support belt according to claim 7, wherein:

said cooperative fastening means of said one type includes loop-pile fastening means;

said cooperative fastening means of said other type includes hook-pile fastening means;

said cooperative fastening means on said one ends of said straps includes hook-pile fastening means; and said cooperative fastening means on said other ends of said strap includes loop-pile fastening means.

9. A lumbar support belt for being worn by a person, comprising in combination:

a laterally elastic support section for engaging the person's back generally in the lumbar region when the belt is worn, said elastic support section having a lower edge and including two elastic panels of substantially equal elasticity and a third elastic panel laterally separating said two elastic panels and of elasticity less than the elasticity of said two elastic panels; and two end panels respectively secured to said elastic support section along laterally opposite ends thereof, each of said end panels including thereon cooperative loop-pile fastening means, one of said end panels having secured thereto cooperative hook-pile fastening means for cooperating with said loop-pile fastening means on the other of said end panels for releasably securing said end panels to one another generally in front of the person when the belt is worn, each of said end panels having a lower edge ascending from said lower edge of said elastic belt section for precluding said end panels from engaging the person's thighs when the belt is worn.

10. The lumbar support belt according to claim 9, further including:

cooperative hook-pile fastening means on each of said laterally separated elastic panel of said elastic support section; and two suspender straps, each of said straps having at one end thereof cooperative hook-pile fastening means for cooperating with said loop-pile fastening means on said end panels for releasably securing said one ends of said straps to said end panels respectively, each said strap having at another end thereof cooperative loop-pile fastening means for cooperating with said hook-pile fastening means on said elastic panels for releasably securing said other ends of said straps to said two laterally separated elastic panels respectively.

* * * * *